United States Patent
Wolfe et al.

[11] Patent Number: 5,676,961
[45] Date of Patent: Oct. 14, 1997

[54] COCKROACH BAIT FEEDING STIMULI

[75] Inventors: James Wolfe, Pleasanton, Calif.; Don Lesiewicz, Edison; Yashpal Mehra, Oldbridge, both of N.J.; Joseph Mares, Valdosta, Ga.

[73] Assignee: The Clorox Company, Oakland, Calif.

[21] Appl. No.: 757,408

[22] Filed: Nov. 27, 1996

Related U.S. Application Data

[62] Division of Ser. No. 304,627, Sep. 12, 1994, Pat. No. 5,607,682.

[51] Int. Cl.$^6$ ............................................. A01N 25/08
[52] U.S. Cl. ........................ 424/410; 424/84; 426/1
[58] Field of Search ................... 424/84, 410, 405; 426/1

[56] References Cited

U.S. PATENT DOCUMENTS

| | | | |
|---|---|---|---|
| 4,049,460 | 9/1977 | Broadbent | 424/84 |
| 4,087,525 | 5/1978 | Lovell . | |
| 4,160,824 | 7/1979 | Tnazuka et al. . | |
| 4,205,066 | 5/1980 | Hennart et al. . | |
| 4,353,907 | 10/1982 | Lovel . | |
| 4,514,960 | 5/1985 | Sears . | |
| 4,657,912 | 4/1987 | Suzuki et al. . | |
| 4,845,103 | 7/1989 | Spaulding et al. . | |
| 4,849,216 | 7/1989 | Andersen . | |
| 4,945,107 | 7/1990 | Minetti . | |
| 4,988,510 | 1/1991 | Brenner et al. | 424/84 |
| 4,990,514 | 2/1991 | Bruey . | |
| 5,021,237 | 6/1991 | Bruey . | |
| 5,126,139 | 6/1992 | Geary | 424/410 |
| 5,271,180 | 12/1993 | Wolfe et al. | 43/131 |
| 5,346,700 | 9/1994 | Stapleton et al. | 424/410 |
| 5,547,955 | 8/1996 | Silverman et al. | 514/275 |

FOREIGN PATENT DOCUMENTS

| | | |
|---|---|---|
| 190 844 A2 | 8/1986 | European Pat. Off. . |
| 598 156 A1 | 5/1994 | European Pat. Off. . |
| 61-106505 | 9/1984 | Japan . |

*Primary Examiner*—John C. Bleutge
*Assistant Examiner*—Robert H. Harrison
*Attorney, Agent, or Firm*—Stephen Kalinchak; Harry A. Pacini

[57] ABSTRACT

The insect bait composition in the present invention is useful for feeding stimuli to induce insects, especially cockroaches, to preferably feed upon said bait composition, which will stimulate insect feeding and successfully compete with other food sources in the environment, said stimulant bait composition having one or more protein sources derived from poultry liver, silkworm pupae and hydrogenated soy protein.

4 Claims, No Drawings

COCKROACH BAIT FEEDING STIMULI

This is a divisional application under 37 C.F.R. § 1.60 of prior application Ser. No. 08/304,627 filed Sep. 12, 1994, now U.S. Pat. No. 5,607,682.

The present invention relates to insect bait compositions useful for feeding stimuli to induce insects to preferably feed upon said bait composition. Therefore, when combined with an appropriate insecticide, the insect feeding upon the feeding stimuli containing compositions of the present invention will ingest the insecticide, which will then cause mortality of the insect.

More particularly, the present invention relates to insect bait compositions which are preferred feeding stimuli for cockroaches, wherein the bait stimuli will be consumed in high quantities by cockroaches under field conditions.

BACKGROUND OF THE INVENTION

Insects, especially cockroaches, are omnivorous insects. These insects typically infest locations that contain sufficient food, moisture and shelter for survival. Cockroaches forage for food randomly and will examine a food prior to ingesting it. If the food does not contain ingredients that stimulate feeding of the insect, the cockroach may continue to forage for appropriate food sources. An avoidance or lack of feeding on a bait containing poisonous material may reduce the effectiveness of the insecticide against cockroaches under field conditions. Therefore, the purpose of this invention is to formulate an insect bait, in particular a cockroach bait, that will be preferentially consumed in high quantities by cockroaches under both laboratory and field conditions.

Research has shown that German cockroaches, for example, cannot detect food from a large distance, that is, greater than five to ten inches. As a result, German cockroaches forage for food primarily along baseboards and behind applicances. As cockroaches encounter a bait station, the insect will examine the bait using this mouth parts and antennae. If the bait meets the cockroach nutritional needs, they may consume the bait. Cockroaches can learn to return to previously investigated food resources. Therefore, cockroach baits must be palatable enough to compete with other food sources in the environment to cause the insect to repeatedly visit the food resource and to ingest a lethal dose of toxicant applied thereto.

DISCUSSION OF THE PRIOR ART

U.S. Pat. No. 4,353,907 relates to amidino hydrazones useful in insect and fire ant bait formulations and compositions in mixture with fatty acids and an edible oil.

U.S. Pat. 4,845,103 relates to solid, non-particulate, non-flowable, non-repellant insecticide bait compositions for household control of cockroaches, comprising a pentadienone hydrazone insecticide compound, a food attractant system and a binder. The food attractant system is a mixture of liquid food selected from molasses, corn syrup, maple syrup, honey and mixtures of two of these foods, and a solid food-oatmeal.

U.S. Pat. 4,657,912 relates to a granular bait composition for control of ants, employing a pyrimidinone derivative in combination with ground pupae of silkworm.

U.S. Pat. No. 4,990,514 relates to insecticide bait compositions for control of cockroaches comprising an insecticide compound, a food attractant system and a flowable binder. The food attractant used in the composition comprises a mixture of liquid food selected from molasses, corn syrup, maple syrup, honey and mixtures of two or more of these food substances.

Japanese Patent Application 61:106505 discloses insect attracting compositions for ants containing as attractant components a mixture of carbohydrate, protein and lipid. Preferably, the carbohydrate is fruit juice, honey, sucrose, sugar, lactose, D-glucose, D-glucosamine, etc. Preferably, the composition is powdered, granular, solid, paste, liquid or gel. The protein source is an animal protein or vegetable protein, the lipid is a vegetable oil or animal oil. Various insect-controlling components are formulated with the attractant composition.

SUMMARY OF THE INVENTION

The purpose of this invention is to formulate a cockroach bait that will be consumed in high quantities by cockroaches under either field or laboratory conditions. German cockroaches forage for resources (food and water). It is the object of the present invention to disclose and provide a bait formulation which will stimulate prolonged insect feeding, particularly in cockroaches, also provided for is a bait that will be consumed. Further, the stimulant bait formulation should not require coverage of the total surface or area where target organisms forage for food and water. It is therefore the primary object of the present invention to disclose and provide a preferred bait composition which will satisfy the cockroach nutritional needs and be consumed as a bait and at the same time palatable enough to compete with other food sources in the environment.

It is another object of the present invention to provide a stimulant bait composition which will stimulate cockroach feeding for long periods of time and into which an active insecticide can be formulated to produce a lethal dose of toxicant in the cockroach.

Other objects of the present invention will be apparent from the following detailed description.

DESCRIPTION OF THE PREFERRED EMBODIMENT

The foregoing objects of the present invention may be accomplished by forming a novel mixture or solution of protein-aceous food material and certain other ingredients, such as carbohydrates and various binding ingredients and carriers, to complete the composition.

The preferred embodiment of the present invention is a feeding stimulant composition comprising on a weight basis
- from about 0% to about 50% proteinaceous food material as a feeding stimuli;
- from about 0% to about 50% vegetable protein as a feeding stimuli/binder;
- from about 0% to about 65% grain food as a feeding stimuli/binder;
- from about 0% to about 30% carbohydrate as a feeding stimuli; and
- from about 0% to about 40% lipid as a feeding stimuli/binder.

An antimicrobial and/or antioxidant agent also may be included. These feeding/bait compositions have been found to be exceedingly effective for consumption by insects, such as cockroaches (*Blattella germanica, Periplaneta americana*) which typically infest locations that contain sufficient food, moisture and shelter for survival.

A more preferred embodiment of this invention is a bait composition comprising on a Weight basis:
- from about 0% to about 50% spray-dried poultry liver;
- from about 0% to about 50% ground silkworm pupae;

from about 0% to about 50% hydrogenated soy protein;

from about 15% to about 65% ground oatmeal;

from about 0% to about 30% high fructose corn syrup; and from about 0% to about 40% partially hydrogenated soy-bean oil.

Examples of other carriers are fish meal, powdered sugar, flour, rice bran oil, corn oil, soybean oil, corn syrup, glucose, krill and the like. The compositions of the present invention are exceedingly effective for stimulating feeding in a variety of cockroach insects and subsequently when used with an insecticide controlling said cockroach population. Examples of other suitable carbohydrates include sucrose, maltose, arabinose, galactose, lactose, glucose, D-glucose, and D-glucosamine.

Silkworm pupae is a by-product of the silk industry obtained during the isolation of silk. Compositions of the invention may readily be prepared by grinding the dry pupae by conventional methods to maximize the yield of 10–60 mesh particles, which is preferred.

Spray drying methods are in the prior art and therefore no detailed exemplification need be given; however, in the interest of clarity, the following brief description of spray drying will be given. Spray drying is unique in that it dries a finely divided droplet by direct contact with the drying medium (usually air) in an extremely short retention time, 3 to about 30 seconds. This short contact time results in minimum heat degradation of the dried product. Drying from a particle generally takes place in two stages, the constant-rate and the falling rate period. The primary drying force is the temperature difference between the surrounding air and the temperature of the particle. This technique is particularly effective in preparing poultry liver useful in the present bait compositions.

Various other protein sources may be used in the present formulation. Animal digest is an acceptable source of animal protein coming from beef, poultry, fish and insect parts. Animal digest also includes internal organ parts obtained as by-products from slaughter house processing of such animals. These animal materials are preferably treated prior to use, as by spray drying, freeze drying and oven drying.

In addition, this development may be formulated with a novel emulsion carrier for the active insecticidal ingredient, preferably a pentadien-3-one substituted amidino hydrazone insecticide as described in U.S. Pat. No. 4,087,525, for example, 1,5-bis($\alpha,\alpha,\alpha$-trifluoro-p-tolyl)-1,4-pentadien-3-one, 4,5,6,7-tetrahydro-1H-1,3-diazepine-2-yl hydrazone;

1,5-(bis($\alpha,\alpha,\alpha$-trifluoro-p-tolyl)-1,4-pentadien-3-one, 4,5,6,7-tetrahydro-1H-1,3-diazepine-2yl hydrazone hydrochloride;

1,5-bis(p-chlorophenyl)-1,4-pentadiene-3-one,4,5,6,7-tetrahydro-1H-1,3-diazepine-2-yl hydrazone hydroiodide; and 1,5-bis(p-chorophenyl)-1,4-pentadiene-3-one,4-phenyl-2-imidazolin-2-yl hydrazone hydriodide. The disclosure of U.S. Pat. No. 4,087,525 is incorporated herein by reference thereto, describing the use of these compounds as insecticides.

Other insecticides can be substituted for the substituted amidino hydrazone insecticide, particularly organophosphates, such as:

chlorpyrifos—O,O-diethyl O-(3,5,6-trichloro-2-pyridinyl) phosphorothioate;

carbamates, such as propoxur-2-(1-Methylethoxy) phenol methylcarbamate;

pyrethroids, such as phenothrin—(3-phenoxyphenyl) methyl 2,2-dimethyl-3-(2-methyl-1-propenyl) cyclopropane carboxylate;

chlorinated hydrocarbons;

fluoroaliphatic sulfonamides, such as sulfluramid-N-ethyl perfluorooctane sulfonamide;

boric acid;

insect growth regulators, such as hydroprene-ethyl (E,E) -3,7,11-trimethyl-2,4-dodecadienoate; and microbially derived compounds, such as avermectin $B_1$ (a mixture of avermectins containing 80% aveermectin $B_{1a}$ (5-O-dimethylavermectin $A_1a(R=C_2H_5)$ and 20% $B_1b$ (5-O-methyl-25-de(1-methylpropyl)-25-(1-methylethyl) avermectin $A_1a(R=CH_3)$.

The lipid phase contains soybean oil, a fatty acid, the active ingredient and an emulsifier and the aqueous phase contains a high fructose corn syrup. Other long chain fatty acids and various lipids would be acceptable substitutes or replacements for the fatty acid and lipid components identified herein.

Therefore, the present invention includes a method for controlling cockroaches comprising applying in the vicinity of their habitat or infested area an insecticidal bait composition comprising an insecticidally effective amount of a substituted amidino hydrazone insecticide or fatty acid salt thereof and the bait/feeding composition containing feed stimulants according to the present invention. Additional edible carriers such as fish meal, sugars, flour and the like may be added and the mixture blended until homogeneous.

Optionally, from about 0.0% to about 2.0% of an antimicrobial agent such as sorbic acid/potassium sulfate, Dowcil™ 200 (cis isomer of 1-(3-chloroallyl)3,5,7-triaza-1-azonia-adamantane chloride), propyl paraben/methyl paraben (propyl p-hydroxybenzoate/methyl p-hydroxybenzoate), Captan (N-(trichloromethylthio)-4-cyclohexane-1,2-dicarboximide), sodium silicate, sodium dehydroacetate and sodium benzoate may be added to inhibit microorganism growth, or from about 0.0% to about 2.0% of an anti-oxidant such as tert-butyl hydroquinone, n-propyl gallate, 3-tert-butyl-4-hydroxyanisol and butylated hydroxy toluene or mixtures thereof may be incorporated during the blending of the composition to improve the storage characteristics of the final compositions, as can other agents such as thickening agents and the like.

The insecticidal composition with the bait according to the present invention can also be present in the form of an aerosol, in which case a co-solvent and a wetting agent are conveniently used, in addition to the propellant. The propellant is suitably a hydrochlorofluorocarbon alkane such as chloro difluoro methane, a non-halogenated alkane such as butane, and the like, carbon dioxide or nitrogen. The following types of formulations can be utilized to apply the formulated bait compositions with or without an effective amount of insecticidal agent: powders, dusts, granulates, solutions, suspensions, emulsions, emusifiable concentrates, pastes, foams, gels, fumigants, atomizing compositions, baits, and aerosols. The formulations of this invention can also be included in insect feeding stations such as bait trays.

The invention is further illustrated by the following non-limiting examples.

Procedure for Bait Compounding

Soybean oil (100 grams) (g), glycerylmonostearate (5 g), soy protein (58.5 g), and oleic acid (10 g) were mixed and heated to approximately 170° F. until all solids had dissolved. Corn syrup (50 g) heated to 140° F. was added to this and mixed to form an emulsion. Spray dried poultry liver (58.5 g), dried and ground silkworm pupae (58.5 g) and oatmeal (150 g) were added to the heated liquid and agitated until uniform. The finished solution was poured into small cups and cooled to room temperature.

TABLE I

FORMULATIONS TESTED

| Ex. No. | Poultry Liver | Silkworm Pupae | Soy Protein | Oatmeal | Corn Syrup | Partially Hydrogenated Soybean oil |
|---|---|---|---|---|---|---|
| 1 | 35.00 | 3.00 | 0.00 | 30.00 | 10.00 | 10.00 |
| 2 | 5.83 | 5.84 | 5.83 | 47.50 | 10.00 | 20.00 |
| 3 | 17.50 | 17.50 | 0.00 | 30.00 | 10.00 | 20.00 |
| 4 | 0.00 | 0.00 | 17.50 | 47.50 | 10.00 | 20.00 |
| 5 | 0.00 | 0.00 | 35.00 | 30.00 | 10.00 | 20.00 |
| 6 | 11.67 | 11.66 | 11.67 | 30.00 | 10.00 | 20.00 |
| 7 | 17.50 | 0.00 | 0.00 | 47.50 | 10.00 | 20.00 |
| 8 | 0.00 | 35.00 | 0.00 | 30.00 | 10.00 | 20.00 |
| 9 | 0.00 | 17.50 | 17.50 | 30.00 | 10.00 | 20.00 |
| 10 | 17.50 | 0.00 | 17.50 | 30.00 | 10.00 | 20.00 |
| 11 | 0.00 | 17.50 | 0.00 | 47.50 | 10.00 | 20.00 |
| 12 | 0.00 | 0.00 | 0.00 | 65.00 | 10.00 | 20.00 |
| 13 | 35.00 | 0.00 | 0.00 | 30.00 | 15.00 | 20.00 |
| 14 | 0.00 | 25.00 | 0.00 | 30.00 | 0.00 | 40.00 |
| 15 | 15.00 | 0.00 | 0.00 | 30.00 | 0.00 | 40.00 |
| 16 | 12.50 | 17.50 | 0.00 | 30.00 | 15.00 | 20.00 |
| 17 | 10.00 | 0.00 | 0.00 | 30.00 | 30.00 | 20.00 |
| 18 | 35.00 | 0.00 | 0.00 | 30.00 | 30.00 | 0.00 |
| 19 | 17.50 | 17.50 | 0.00 | 30.00 | 30.00 | 0.00 |
| 20 | 0.00 | 35.00 | 0.00 | 30.00 | 10.00 | 20.00 |
| 21 | 7.50 | 17.50 | 0.00 | 30.00 | 0.00 | 40.00 |
| 22 | 35.00 | 0.00 | 0.00 | 30.00 | 0.00 | 30.00 |
| 23 | 0.00 | 35.00 | 0.00 | 30.00 | 30.00 | 0.00 |
| 24 | 10.00 | 0.00 | 0.00 | 30.00 | 15.00 | 40.00 |

Active ingredient target is 2% by weight. Therefore, the compositions of the cited bait formulations sum to 98%, with the remainder available for the addition of active ingredient.

Explanation of Formulations Without Active Ingredient

For the above feeding stimulant tests, the experimental baits did not contain active ingredients, since the consumption of active ingredient would have inhibited further insect feeding. The test length was set to 3 days for each formula to collect sufficient feeding data. Presence of an active ingredient would have increased variability by causing mortality in the insect population feeding on the bait formulation. Subsequent tests with the substituted amidino hydrazone active ingredient indicated that the insects fed upon the test baits containing active ingredient, notwithstanding the presence or absence of the active ingredient.

Explanation of Feeding Data

The feeding data were measured as weight loss of bait, relative to the mass of cockroaches in each container. The total mass of cockroaches used for each test could not be precisely controlled. A cockroach population of higher mass (more insects, higher proportion of adult insects) is expected to consume more bait than a smaller mass. In addition, consumption tests were run for three days. Therefore, the consumption of bait in each test was divided by three to report a standard, 1 day consumption figure.

The feeding data ratios were calculated as the ratio of feeding on the experimental bait to that of a standard bait base. The feeding data are presented in Table II.

TABLE II

| Ex. No. | Consumption Lab Strain (mg/g roach/day) | Consumption Field Strain (mg/g roach/day) | Ratio of Feeding (mg Formula per mg of Control) LAB STRAIN | Ratio of Feeding (mg Formula per mg of Control) FIELD STRAIN |
|---|---|---|---|---|
| 1.0 | 13.15 | 13.67 | 1.48 | 3.87 |
| 2.0 | 6.24 | 7.07 | 0.59 | 2.42 |
| 3.0 | 7.56 | 10.17 | 0.92 | 2.63 |
| 4.0 | 2.79 | 3.91 | 0.23 | 0.62 |
| 5.0 | 6.53 | 5.45 | 0.59 | 0.81 |
| 6.0 | 8.12 | 9.40 | 0.84 | 3.00 |
| 7.0 | 10.75 | 9.27 | 0.91 | 1.81 |
| 8.0 | 4.17 | 3.97 | 0.42 | 0.97 |
| 9.0 | 2.09 | 2.32 | 0.17 | 0.41 |
| 10.0 | 9.44 | 11.06 | 0.88 | 1.77 |
| 11.0 | 3.54 | 4.03 | 0.30 | 0.57 |
| 12.0 | 0.11 | 5.50 | 0.01 | 0.85 |
| 13.0 | 22.28 | 21.53 | 3.18 | 5.69 |
| 14.0 | 9.68 | 16.91 | 0.52 | 5.20 |
| 15.0 | 12.64 | 19.52 | 0.89 | 3.22 |
| 16.0 | 21.07 | 24.40 | 2.43 | 5.93 |
| 17.0 | 28.48 | 18.41 | 5.28 | 5.60 |
| 18.0 | 33.41 | 20.50 | 5.22 | 3.97 |
| 19.0 | 32.93 | 31.34 | 5.68 | 11.80 |
| 20.0 | 17.24 | 20.21 | 1.22 | 8.30 |
| 21.0 | 14.72 | 29.74 | 1.41 | 7.80 |
| 22.0 | 16.52 | 21.91 | 1.29 | 5.22 |
| 23.0 | 26.88 | 19.36 | 3.46 | 4.77 |
| 24.0 | 26.55 | 26.73 | 3.59 | 6.85 |

The results of these experiments demonstrate the improved effectiveness as feeding stimuli of the compositions of this invention. Therefore, by utilizing the compositions of this invention, together with an insecticidally effective amount of insecticidal compound, the efficacy of the insecticidal compound can be increased where the mode of application of the insecticide depends upon the insect species feeding upon a source or bait containing the insecticide.

What is claimed is:

1. A method of combatting cockroaches which comprises applying in the vicinity of their habitat a cockroach bait comprising an insecticide and an insect bait feeding stimulant composition, said composition comprising on a weight basis:

from about 5% to about 50% of at least one animal protein;

from about 5% to about 50% of a vegetable protein;

from about 15% to about 65% of a grain food;

from about 0% to about 30% of a carbohydrate;

from about 0% to about 40% of a lipid; and from about 0% to about 2.0% of an antimicrobial agent, an antioxidant or mixture thereof.

2. The method of claim 1 wherein the animal protein is animal digest.

3. The method of claim 1 wherein the animal protein is selected from the group consisting of spray dried poultry liver, ground silkworm pupae and combinations thereof; wherein said vegetable protein is soy protein; wherein said grain food is oat meal; wherein said carbohydrate is corn syrup; and wherein said lipid is soybean oil.

4. The method of claim 1 wherein the insecticide is selected from the group consisting of organophosphates, chlorpyrifos, carbamates, pyrethroids, chlorinated hydrocarbons, fluoroaliphatic sulfonamides, boric acid, insect growth regulators, and avermectins.

* * * * *